United States Patent
Eichardt et al.

(12) 
(10) Patent No.: US 6,545,757 B1
(45) Date of Patent: Apr. 8, 2003

(54) ATOMIZING DEVICE FOR DISSOLVED AND SOLID SAMPLES

(75) Inventors: Klaus Eichardt, Buergel (DE); Steffen Lindner, Jena (DE)

(73) Assignee: Analytik Jena AG, Jena (DE)

( * ) Notice: Subject to any disclaimer, the term of this patent is extended or adjusted under 35 U.S.C. 154(b) by 8 days.

(21) Appl. No.: 09/830,055

(22) PCT Filed: Aug. 5, 2000

(86) PCT No.: PCT/EP00/07616

§ 371 (c)(1), (2), (4) Date: Jun. 20, 2001

(87) PCT Pub. No.: WO01/14861

PCT Pub. Date: Mar. 1, 2001

(30) Foreign Application Priority Data

Aug. 24, 1999 (DE) .......................... 199 40 095

(51) Int. Cl.[7] .......................... G01J 3/443; G01N 21/74
(52) U.S. Cl. ........................ 356/312; 356/311
(58) Field of Search ................ 356/307, 311, 356/312, 300

(56) References Cited

U.S. PATENT DOCUMENTS

| | | | |
|---|---|---|---|
| 4,834,536 A | 5/1989 | Tamm et al. ............... 356/312 |
| 5,148,234 A | * 9/1992 | Tamm et al. ............... 356/312 |
| 5,249,028 A | * 9/1993 | Ziegler ....................... 356/312 |

FOREIGN PATENT DOCUMENTS

| | | |
|---|---|---|
| DE | 22 25 421 C2 | 5/1982 |
| DE | 21 65 106 C2 | 2/1984 |
| DE | 32 04 873 C2 | 6/1985 |
| DE | 39 24 839 A1 | 4/1990 |
| DE | 42 43 766 A1 | 6/1994 |
| DE | 42 43 767 C2 | 8/1996 |
| DE | 42 43 766 C2 | 10/1996 |
| DE | 296 12 065 | 10/1996 |
| EP | 0 363 457 B1 | 3/1989 |
| EP | 0 364 539 B1 | 3/1989 |
| GB | 2 159 028 A | 11/1985 |
| JP | 09-068493 A | * 3/1997 |

OTHER PUBLICATIONS

*English Abstract of DE 21 65 106 C2.
*English Abstract of EP 0 364 539 B1.
*English Abstract of DE 42 43 766 C2.
*English Abstract of DE 22 25 421 C2.
*English Abstract of DE 39 24 839 A1.
*English Abstract of EP 0 363 457 B1.
*English Abstract of DE 42 43 767 C2.
*English Abstract of DE 32 04 873 C2.
Hideaki Koizumi, High Gas Temperature Furnace for Species Determination of Organometallic Compounds with a High Pressure Liquid Chromatograph and a Zeeman Atomic Absorption Spectrometer, Analytical Chemistry, vol. 51, No. 3, Mar. 1979.
Article: H. Schulze, Überlingen, New Possibilities of Use of Graphite Tube—Atom Absorption—Spectroscopy by the Use of Micro computer controlled Programming, GIT Fachz, Lab. 23, Jg. 1/79, with English Abstract.

* cited by examiner

*Primary Examiner*—John Juba, Jr.
(74) *Attorney, Agent, or Firm*—Reed Smith LLP (57) ABSTRACT

Atomizing device for atomic absorption spectroscopy according to the Zeeman method, wherein a tubular atomizing furnace which is transversely heated via wings and with horizontally oriented furnace tube is located with its furnace wings between vertically arranged electrodes for examination of liquid specimens fed from the top and for examination of solid specimens fed from the side, and the vertically oriented atomizing furnace is located laterally between magnetic poles.

9 Claims, 11 Drawing Sheets

ATOMIZING DEVICE FOR DISSOLVED AND SOLID SAMPLES

CROSS-REFERENCE TO RELATED APPLICATIONS

This application claims priority of German Application No. 199 40 095.4, filed Aug. 24, 1999 and International Application No. PCT/EP00/07616, filed Aug. 5, 2000, the complete disclosure of which is hereby incorporated by reference.

BACKGROUND OF THE INVENTION

1. a) Field of the Invention

In the field of graphite furnace atomic absorption spectroscopy (GF-AAS analysis), tubular furnace bodies and atomizing furnaces based on graphite and Zeeman magnetic field arrangements for compensation of unwanted measurement signals are state of the art. In this connection, extensive descriptions are contained in DE 4243766 C2, DE 4243767 C2, EP 0364539 B1, EP 0363457 and DE 2165106 C2.

2. b) Description of the Prior Art

Generally, a distinction is made between longitudinally heated furnace bodies and transversely heated furnace bodies, wherein separate specimen carriers or platforms, as they are called, or specimen carriers which are connected with the furnace body can be provided in the interior of the respective furnace part. The geometry in the transversely heated furnace bodies has clear analytic and economic advantages over the longitudinally heated type.

For dissolved (liquid) and solid specimens, it is state of the art in GF-AAS analysis to use separate atomizing devices associated with and adapted to the shape and type of specimen and containing either a transversely heated or a longitudinally heated furnace body. Consequently, for example, a laboratory having to analyze both forms or types of specimen must be equipped with two different complete systems of atomic absorption spectrometers, including the accessory units, e.g., peripheral equipment for the specimens.

Typically, the specimens are introduced into the center of the interior space of the furnace body by means of automatic feeders, also known as specimen feeders. In the case of dissolved specimens, the furnace bodies are charged vertically or diagonally from the top.

Solid specimens, on the other hand, are initially deposited outside the furnace on a spoon-like graphite specimen carrier and are quantified by determining the weight of the specimen. The specimen carrier with the specimen is then inserted into the atomizing device approximately horizontally via side openings.

Further, it is conventional in GF-AAS analysis to utilize the Zeeman effect, as it is called, for background compensation. Systems using a procedure of this type are known, for example, from EP 0364539 B1, EP 0363457 B1 and DE 2165106 C2.

EP 036357 B1 and DE 2165106 C2 disclose atomic absorption spectrometers in which a furnace through which a measurement light bundle is radiated is arranged in the air gap of an electromagnet for generating the Zeeman effect.

In this connection, DE 21655106 C2 discloses a GF-AAS atomizing device with Zeeman magnets which are arranged transversely relative to the furnace tube axis, wherein it is not possible to use transversely heated furnace bodies.

It is disadvantageous that the closed, transversely heated construction of the atomizing device and the magnetic poles described in EP 036357 B1 do not permit horizontal feeding of solid specimens, but only permit dissolved specimens to be inserted vertically from above via a fill opening. On the one hand, the longitudinally arranged, bulky magnetic poles must be moved up very close to the front end faces of the furnace tube in order to realize the maximum magnetic field strength of approximately 1 Tesla needed for analysis; on the other hand, however, because of this very circumstance, the field of use for transversely heated furnace tubes, which are so advantageous in terms of analysis, in combination with a longitudinal magnetic field arrangement, is limited only to dissolved specimens.

OBJECT AND SUMMARY OF THE INVENTION

It is the primary object of the invention to provide an atomizing device for an atomic absorption spectrometer which is outfitted with transversely heated furnace bodies and with an electromagnet for background correction using the Zeeman effect and which is accordingly equally suited to the analysis of solid and dissolved specimens.

This object is met by an atomizing device for atomic absorption spectroscopy according to the Zeeman method, wherein a tubular atomizing furnace which is transversely heated via wings and with horizontally oriented furnace tube is located with its furnace wings between vertically arranged electrodes for examination of liquid specimens fed from the top and for examination of solid specimens fed from the side.

According to the invention, an atomizing device for dissolved specimens as well as solid specimens is realized in that a transversely heated furnace tube is arranged in vertically disposed electrodes by means of its contact pieces and the contact pieces of the furnace are provided with centrally supported bore holes for introducing dissolved specimens, for supplying and discharging protective gases, and for detecting tube radiation for purposes of controlling the temperature of the furnace.

Due to this vertical placement of the transversely heated furnace, it is possible, first, to provide the necessary free space for the magnetic poles of a transversely oriented Zeeman magnetic field arrangement which are to be moved up close to the furnace and, second, the front areas of the tubular part of the furnace are kept free such that a horizontal insertion opening for solid specimens which can also be closed periodically by an optical window can be formed on one side, preferably on the left-hand front side of the furnace.

Another step, according to the invention, for providing the necessary free space for insertion of solid specimens is the asymmetric arrangement of the geometric centers of the furnace and magnetic poles relative to one another.

Further, according to the invention, the fill openings for dissolved and solid specimens are outfitted in a simple manner with exchangeable graphite adapters. In this way, quick geometric adaptation to the respective specimen feeders in use can be carried out and the duct not in use can be closed quickly on the one hand and, on the other hand, a possibility is provided for simple cleaning without completely disassembling the atomizing device.

In particular, the inventive solution has the advantages of the Massman furnace technique with Zeeman magnetic field for solid and dissolved specimens which essentially comprise a half-closed atomizer with two tubular furnace parts adapted to the possible specimen forms and separate outer and inner protective gas flows. Also, the exchangeable graphite parts—two for the furnace tube and three for duct adapters—which are adapted to the specimen form are designed as graphite closing parts which can be produced inexpensively and exchanged in a simple manner.

BRIEF DESCRIPTION OF THE DRAWINGS

The invention and its advantages are described more fully with reference to the schematic drawings mentioned below.

DESCRIPTION OF THE PREFERRED EMBODIMENTS

Figure 1:
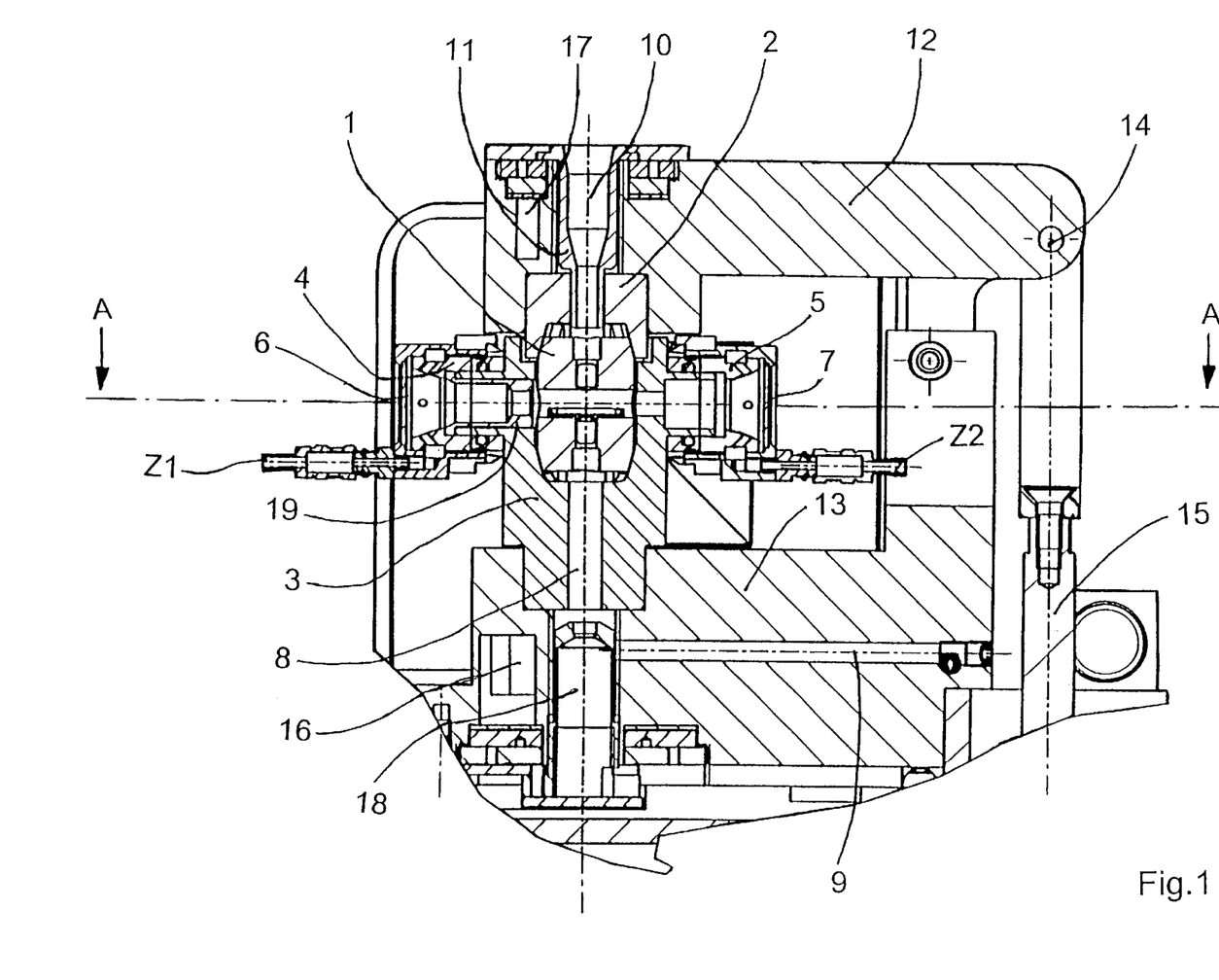
FIG. 1 shows a longitudinal section through the atomizing device with:
- atomizing furnace 1;
- upper electrode 2;
- lower electrode 3;
- right/left window connection pieces 4, 5;
- right/left furnace windows 6, 7;
- bore hole in lower electrode 8;
- outer protective gas duct 9;
- pipetting opening 10;
- pipetting insert and adapter 11;
- housing parts 12, 13;
- hinge between housing parts 14;
- pneumatic actuation element 15;
- cooling ducts 16, 17;
- temperature sensor 18;
- liquid adapter 19;
- furnace tube axis A;
- feed pipe for inner gas flows Z1, Z2.

FIG. 1 shows a longitudinal section through an atomizing device, according to the invention, with a Zeeman magnet, not shown.

The atomizing furnace 1 which is shown in detail in additional drawings is transversely heated and arranged vertically between an upper electrode 2 and a lower electrode 3. Window connection pieces 4 and 5 and furnace windows 6 and 7 adjoin the lower electrode 3 laterally, wherein each furnace window 6 and 7 has a feed pipe Z1, Z2 for supplying inner gas flows.

A liquid adapter 19 is provided in the window connection piece 6; this liquid adapter 19 ensures symmetric ratios for the inner gas flows and is removed from the side in solids operating mode for better feeding of solid specimens.

The lower electrode 3 further has a bore hole 8 through which protective gas is moved up from below to the atomizing furnace via an outer gas duct 9. Further, the furnace temperature is detected via this bore hole by means of a temperature sensor 18 arranged below this bore hole 8.

In liquids operating mode, an upper pipetting opening 10 which is also used to feed the liquid specimens via a specimen feeder device, not shown, forms the output of the outer protective gas flow fed via bore hole 8 and for the inner scavenging gas flows. In liquids operating mode, a pipetting insert 11 which is accessible from the top is located in this opening.

The arrangement is enclosed by two housing parts 12, 13, wherein the upper housing part 12 can be flipped up via a hinge 14 for purposes of exchanging the atomizing furnace 1. A pneumatic actuation element 15 is advantageously provided for actuation.

Curved cooling ducts 16, 17, which are only indicated schematically, are provided in housing parts 12, 13 and are supplied via cooling connection pieces, not shown.

In solids operating mode, which will be discussed with reference to additional views, a blind insert extending up to the furnace body is provided instead of the pipetting insert 11. This blind insert can be a closing plug as is shown, for example, in FIG. 8 by reference number 32.

Figure 2:
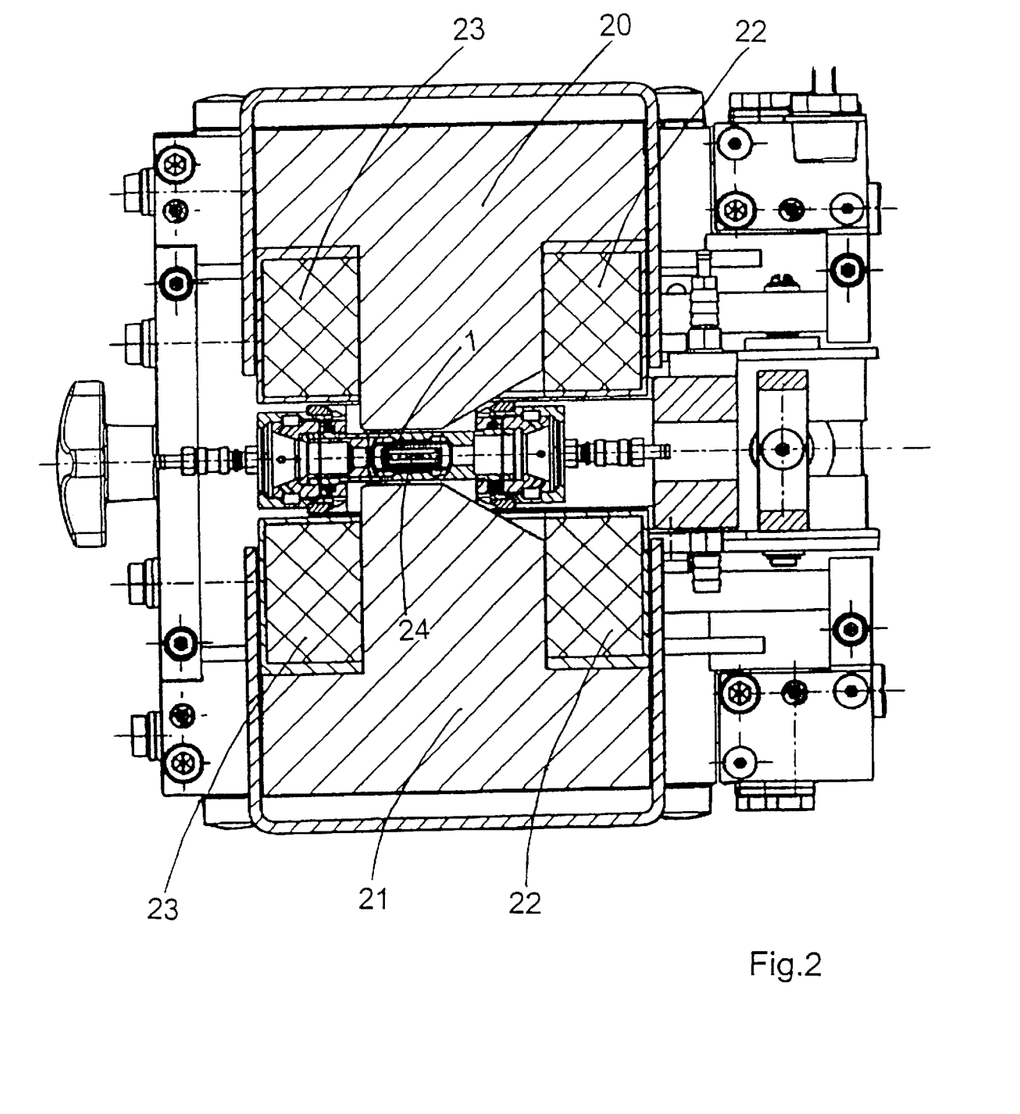
FIG. 2 shows a cross section along the furnace tube axis A with:
- magnetic poles 20, 21;
- coils 22, 23;
- platform 24.

FIG. 2 shows a cross section along the line of the furnace tube axis A according to FIG. 1 viewed in the direction of the arrow.

This Figure shows magnetic poles 20, 21 which laterally enclose the furnace body of the atomizing furnace 1 and coils 22, 23 which are guided up to the furnace body in an optimal manner. It can also be seen that the furnace body is advantageously arranged not in the center axis of the magnetic poles, but asymmetric thereto.

Additional elements have already been mentioned with reference to FIG. 1. Also, a top view shows a platform 24 in the furnace tube for holding the liquid specimen.

Figure 3:
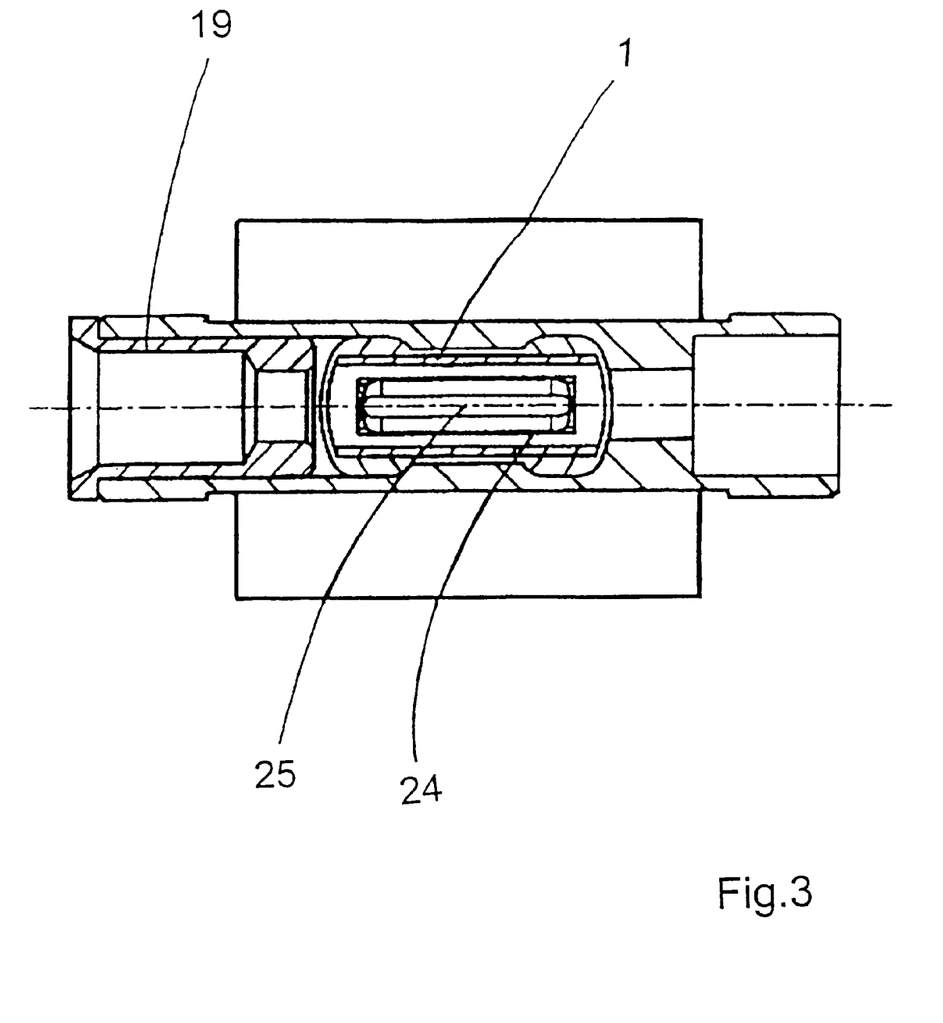
FIG. 3 is a magnified view showing a section from FIG. 2 with:
- cut out 25 in platform 24.

FIG. 3 show a magnified section of FIG. 2, but without external parts and magnets. It can be seen that the platform 24 has a cutout 25 in the interior which receives the dissolved specimen. The liquid adapter 19 which is used only in liquids operating mode can also be seen clearly.

Figure 8:
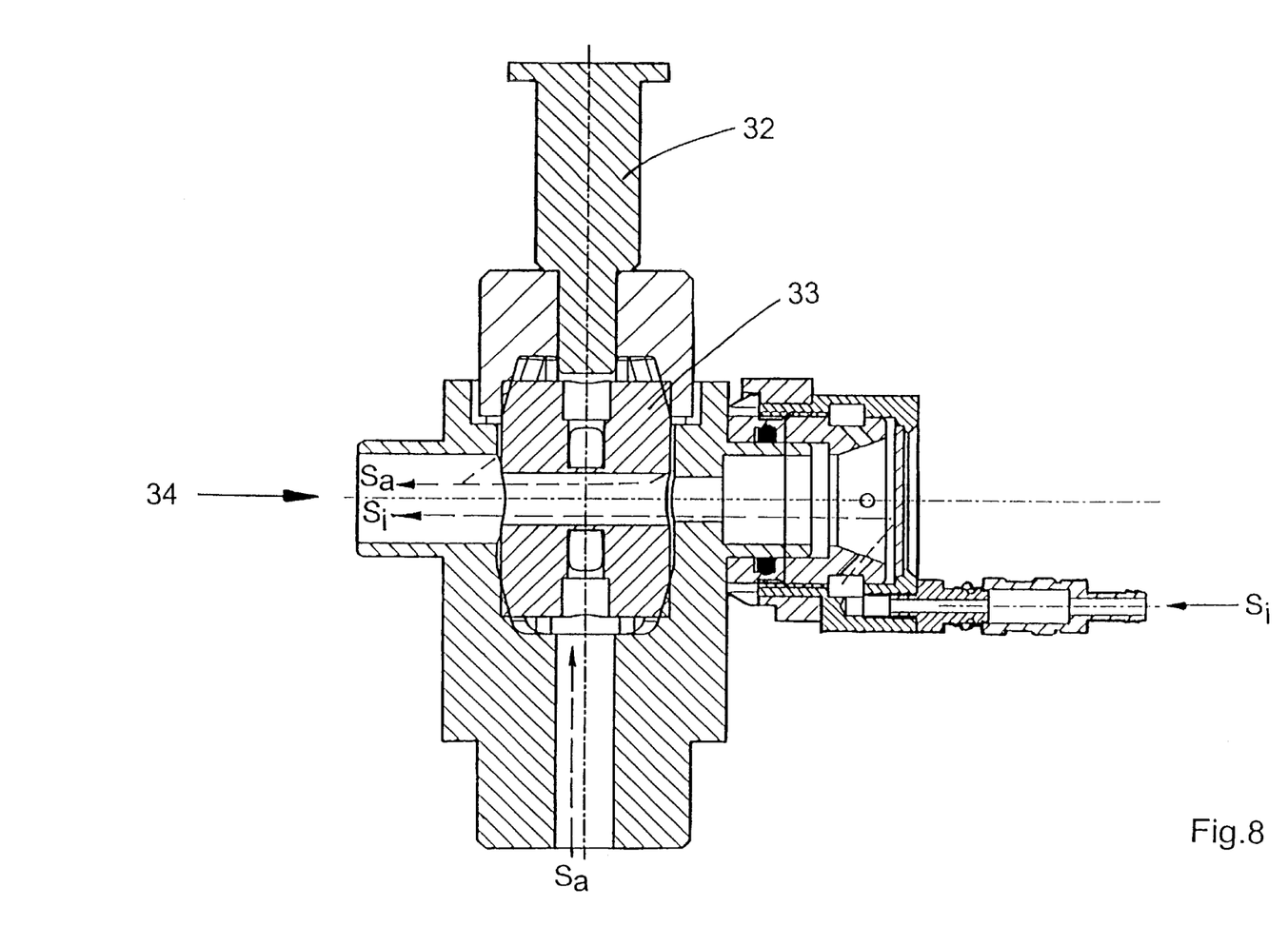
FIG. 8 is a sectional view of the atomizing device for solid specimens with blind insert and adapter 32;
- atomizing furnace 33 for solid specimens;
- feed duct 34 for solid specimens.

It is only in the liquids operating mode that the platform 24 makes up a component part of the tube of the atomizing furnace 1; it is replaced in the solids mode by another construction as shown in FIG. 8 by reference number 33, as will be described in the following.

Figure 4:
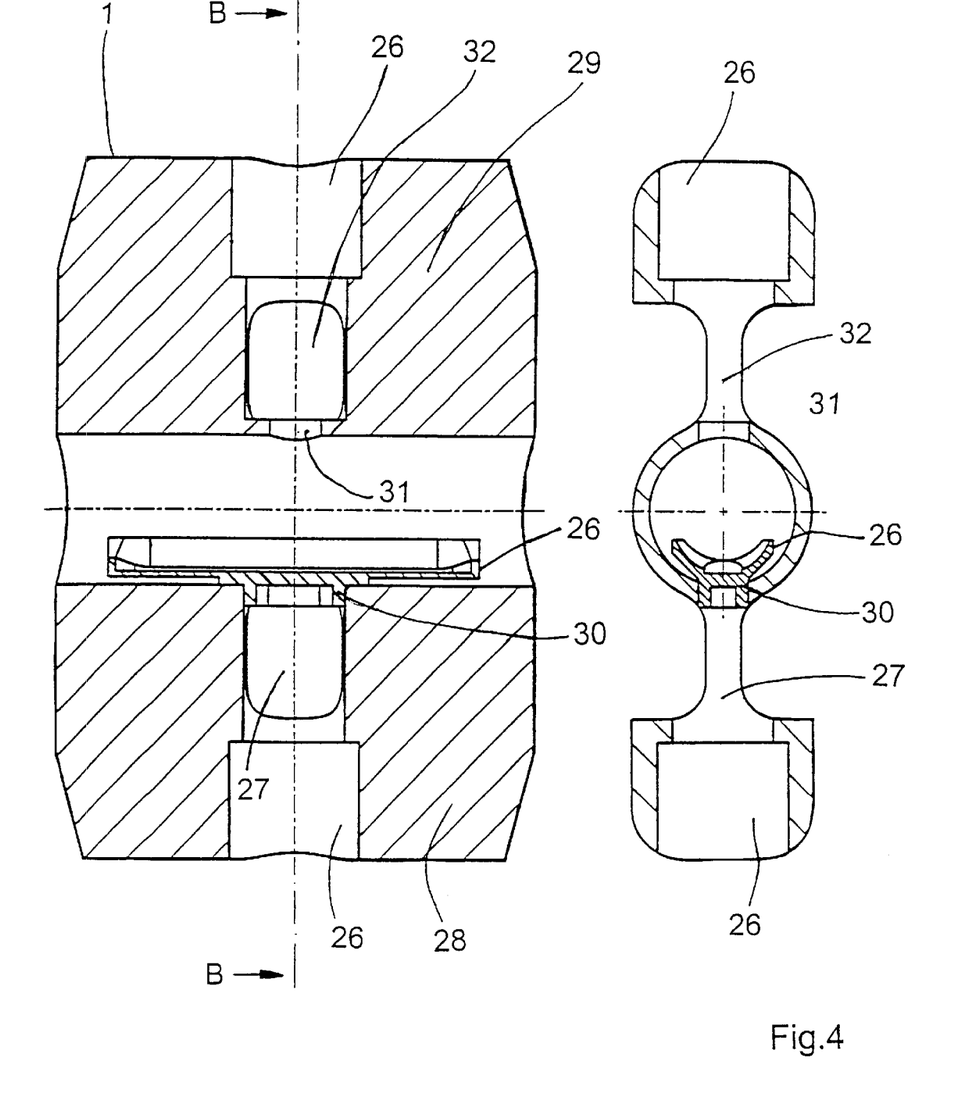
FIG. 4 shows a longitudinal section through the atomizing furnace with dissolved specimens;
- longitudinal bore holes 26;
- openings 27, 32;
- furnace wings 28, 29;
- platform base 30;
- bore hole 31;
- section axis B.

FIG. 4 shows a longitudinal section through the atomizing furnace 1 in the liquids mode and a side view from direction B in which is shown a lower longitudinal bore hole 26 for feeding an external protective gas duct which penetrates the tapering furnace vane or wing 28 in openings 27 and through which the protective gas flows exit and can then continue to flow from the outside through the furnace body 1. The bore hole 26 is closed at its upper end by the inserted foot or base 30 of the platform 24. An upper bore hole 31 is used for feeding liquid specimens.

The outer protective gas flow enters again partially through openings 32 which are provided in the upper wing 29 similar to the openings 27 in the lower wing 28 and flows upward out of the pipetting opening 11 (FIG. 1).

Figure 5:
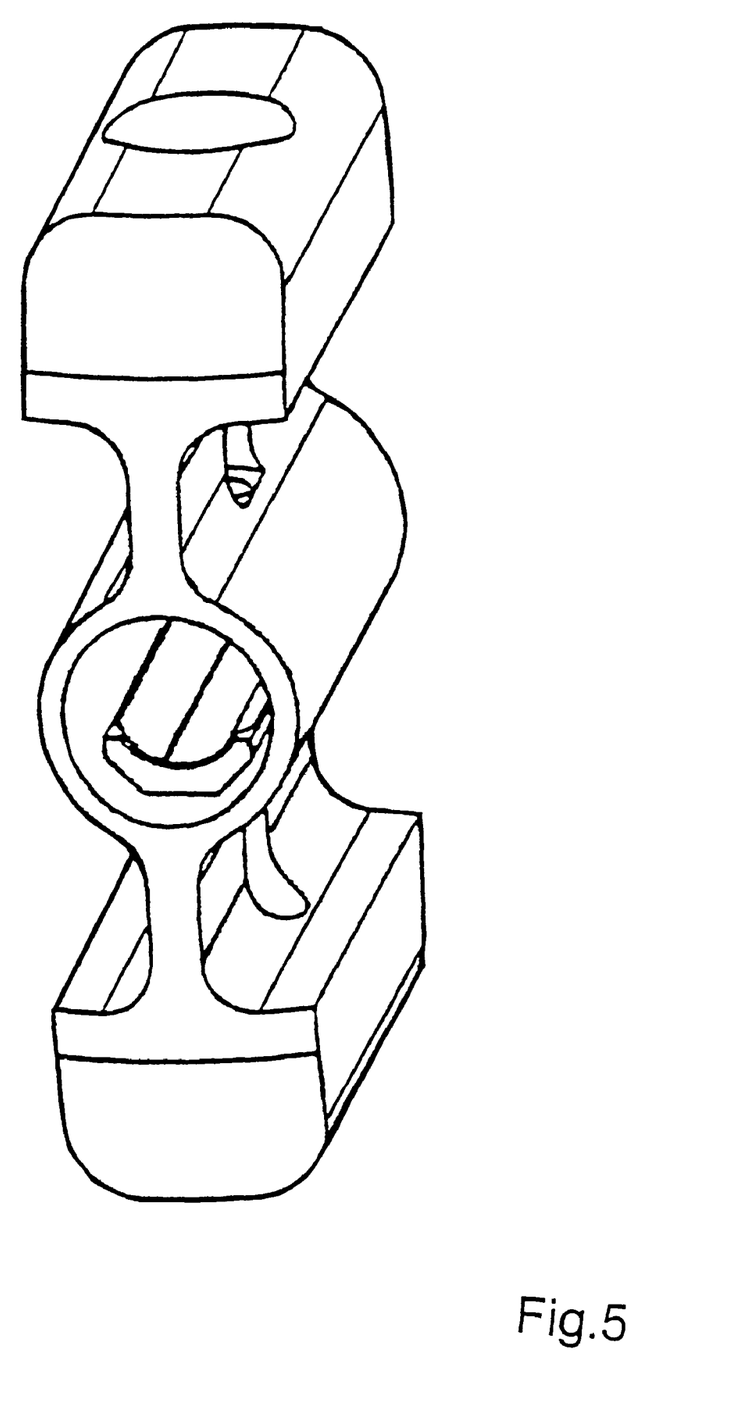
FIG. 5 shows a three-dimensional view of the atomizing furnace with dissolved specimens.

In FIG. 5, the atomizing furnace 1 according to FIG. 4 is shown in a three-dimensional view obliquely from the side.

Figure 6:
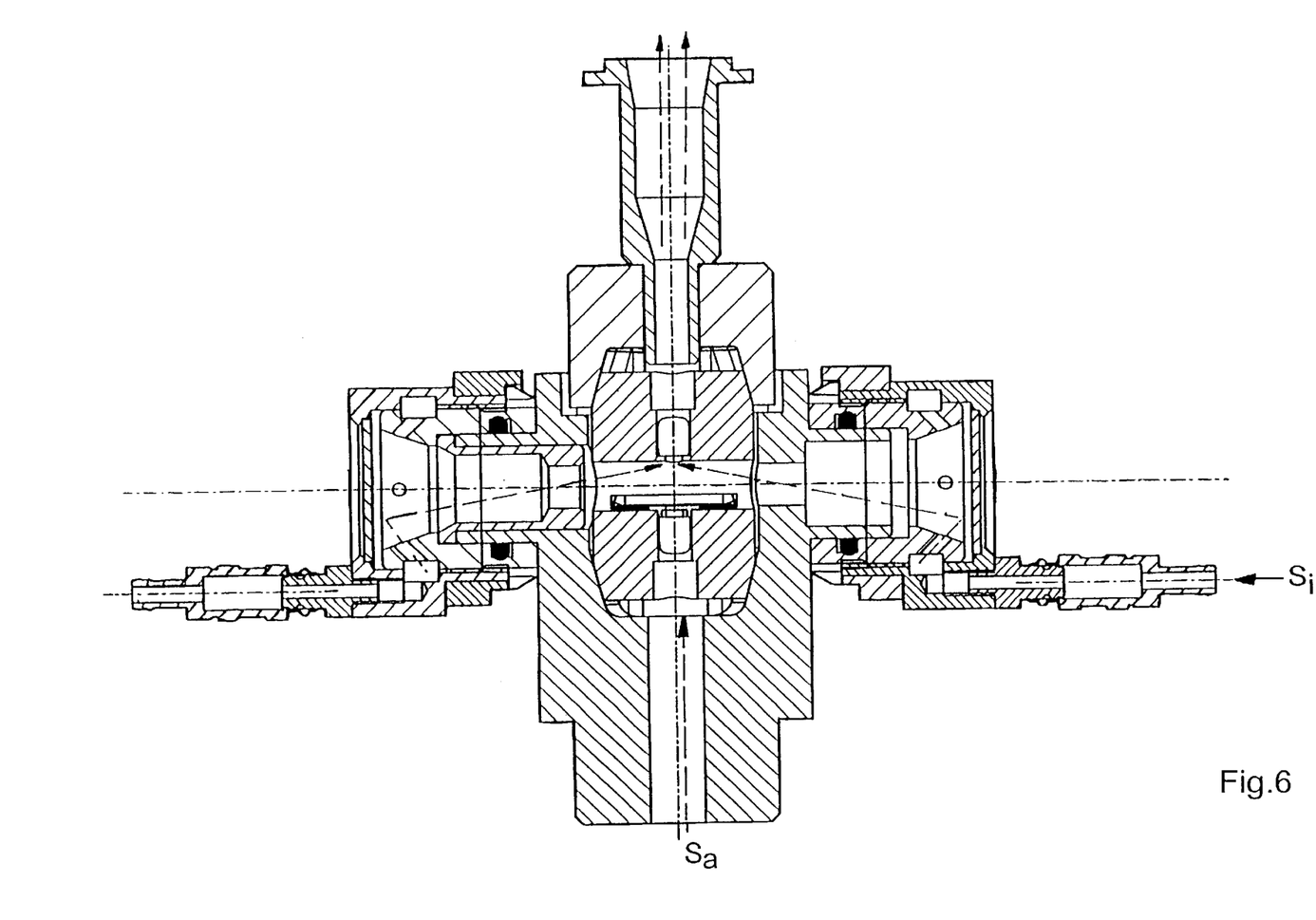
FIG. 6 shows a section from FIG. 1 showing the path of protective gas flows:
- outer protective gas flow Sa;
- inner protective gas flows Si.

FIG. 6 shows a portion of FIG. 1 indicating the directions of the outer protective gas flow Sa and inner protective gas flows Si.

FIG. 8 shows the atomizing device for solids analysis in section with the above-mentioned blind insert 32 for closing the upper half of the furnace when the liquid adapter 19 is removed. Further, a modified atomizing furnace 33 is provided which contains no specimen platform 24 with base 30.

Figure 10:
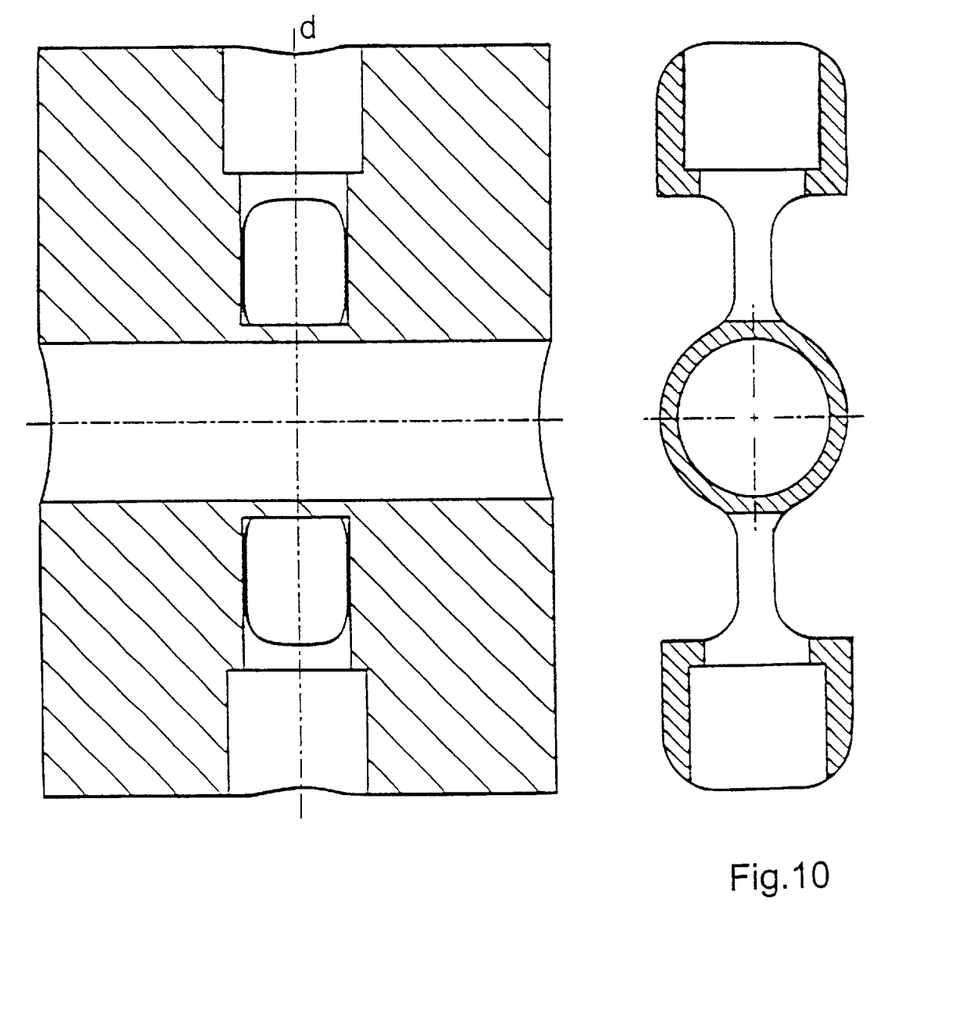
FIG. 10 shows a view of a longitudinal section through the atomizing furnace for solid specimens.
Figure 11:
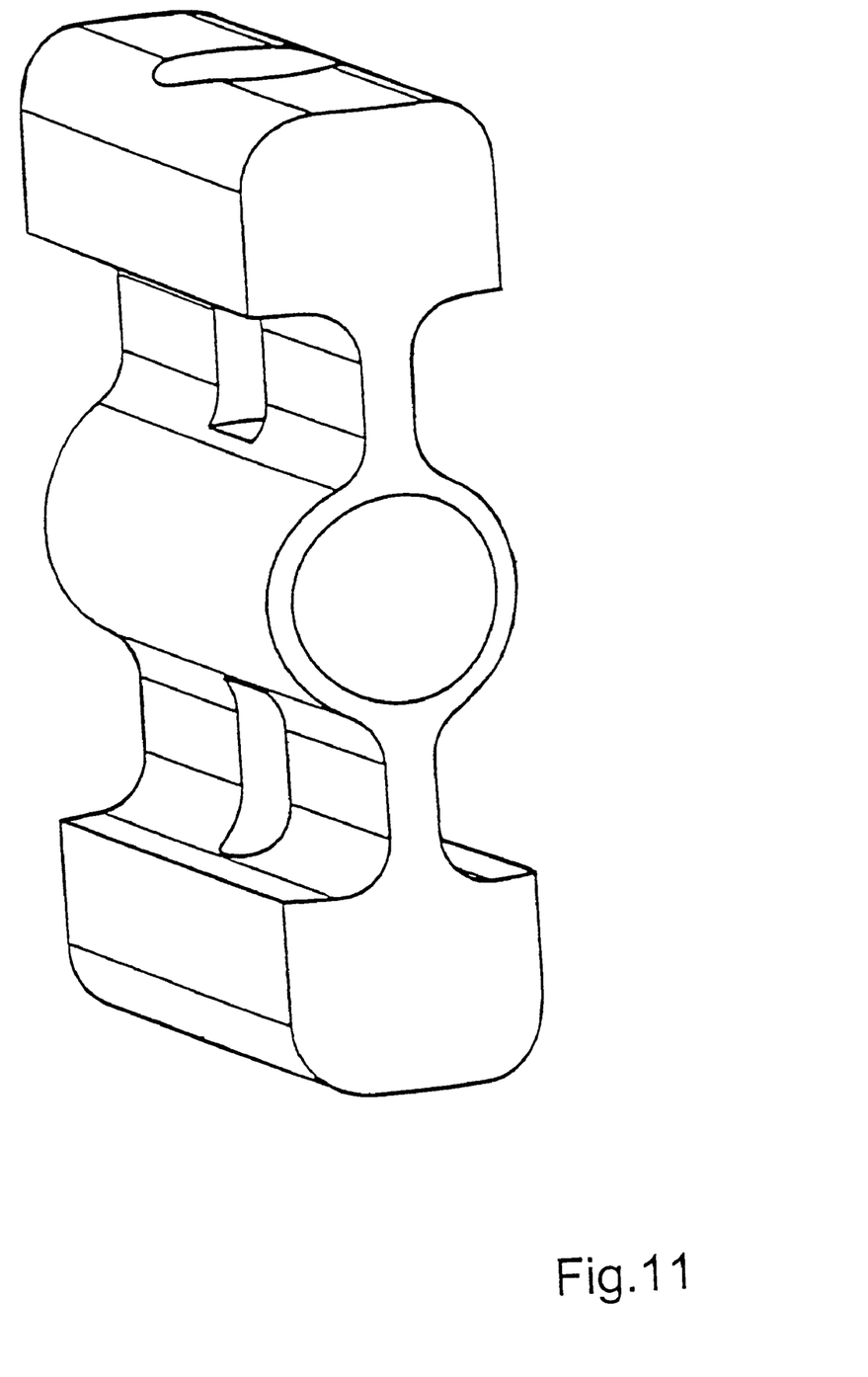
FIG. 11 shows a three-dimensional view of the atomizing furnace for solid specimens.

As is shown in FIG. 10 and FIG. 11, the latter is constructed in a known manner with two wings and is transversely heated and has, in the vicinity of the furnace tube, a tapering longitudinal cut along section line d in the first longitudinal section. The bore holes 26, 31 are provided as was shown in FIG. 4, but in this case do not extend into the furnace tube.

Figure 7:
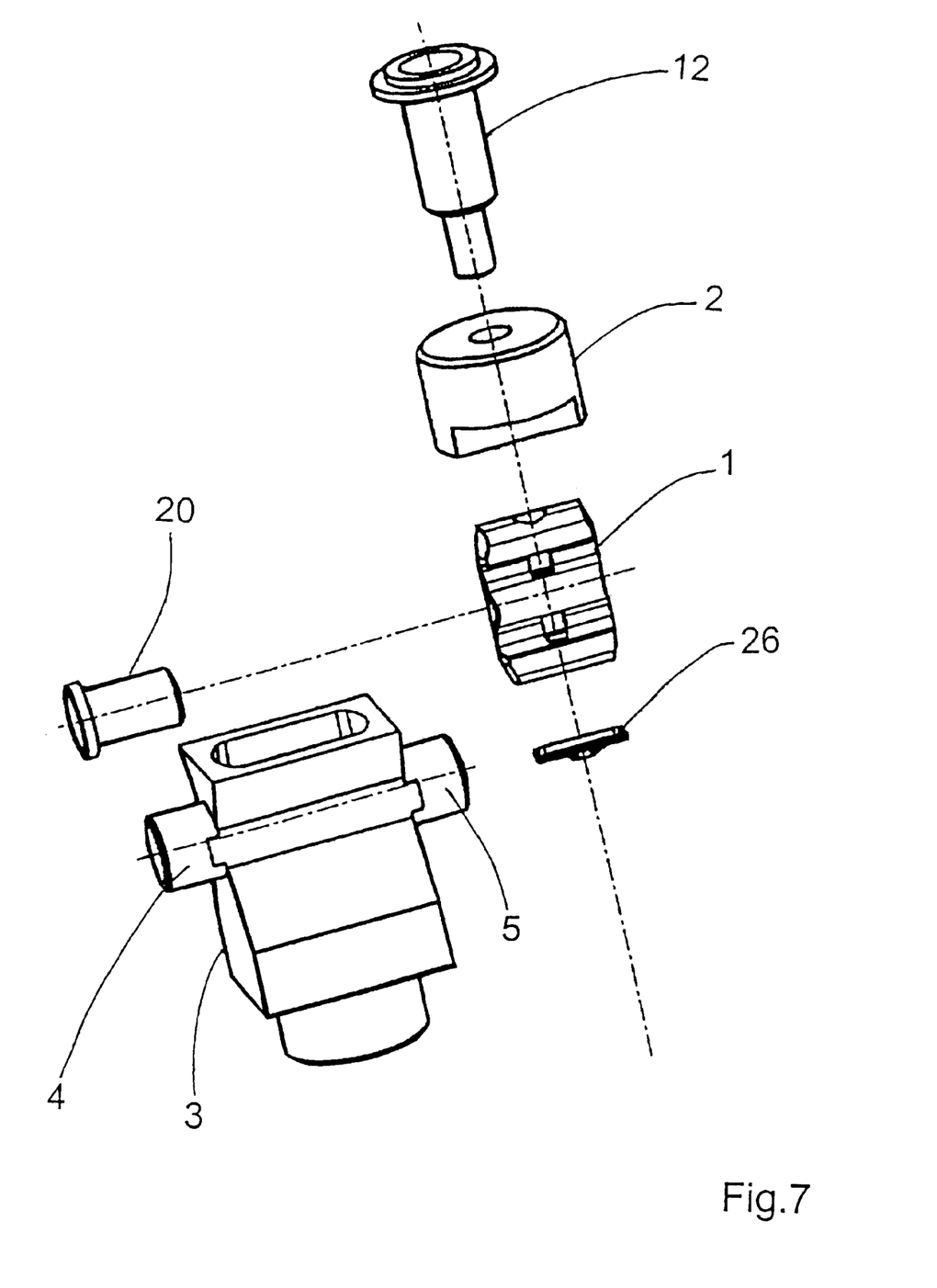
FIG. 7 shows an exploded view of the elements of the atomizing device for dissolved specimens.

Charging is carried out from the side via the larger opening of the window connection piece 4 and a feed duct 34 (see FIG. 7 and FIG. 8). The furnace window subassembly 6 is not attached to the atomizing device 1 for solids analysis; accordingly, both the inner and outer protective gas flows Si, Sa can exit laterally via the feed duct 34.

Figure 9:
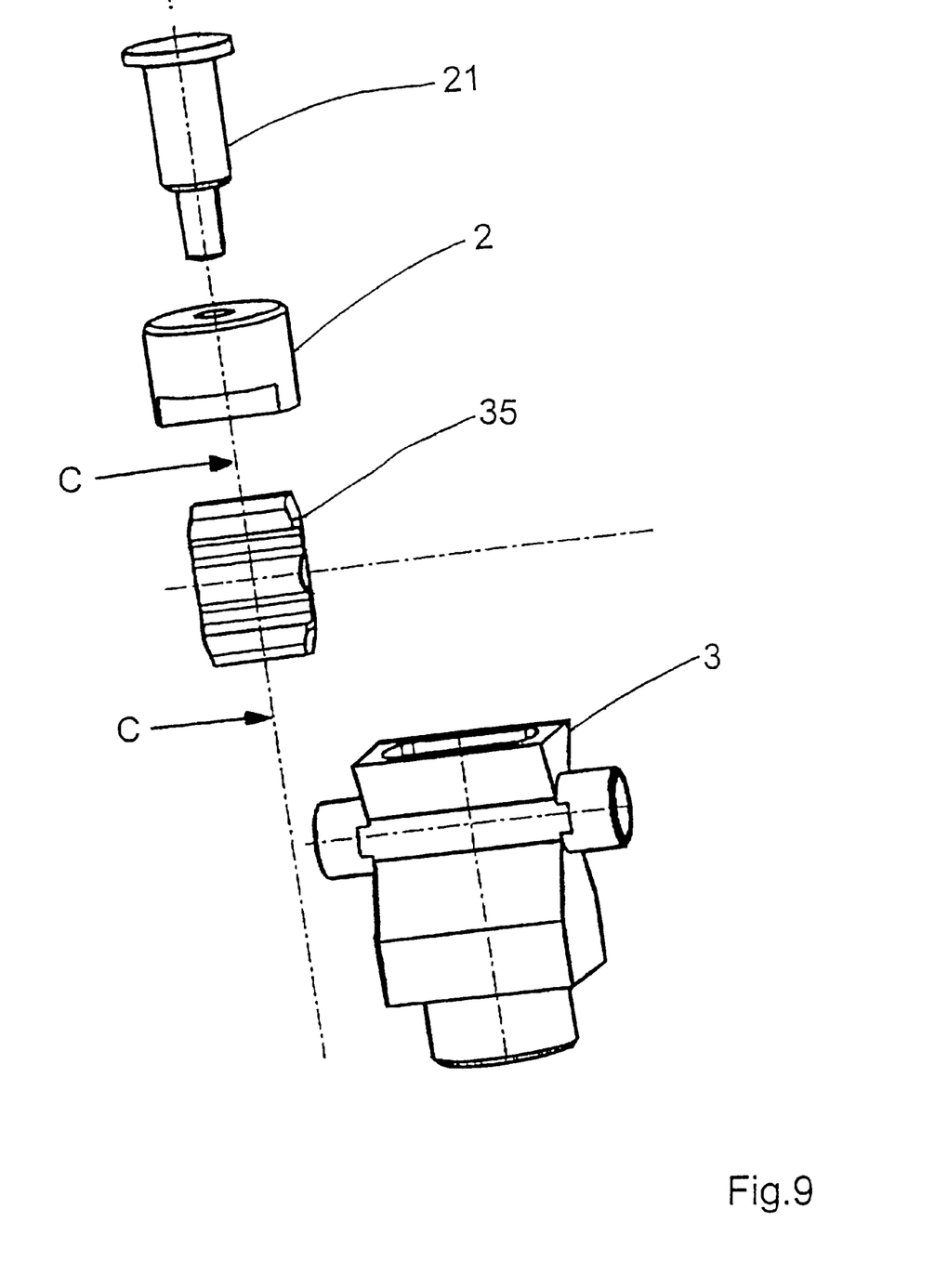
FIG. 9 shows an exploded view of the elements of the atomizing device for solid specimens.

FIG. 9 shows an exploded view of the elements of the atomizing furnace for solid specimens according to FIG. 8.

FIG. 10 shows two longitudinal sections through the atomizing furnace for solid specimens.

FIG. 11 shows the atomizing furnace for solid specimens according to FIG. 10 in a three-dimensional view obliquely from the side.

While the foregoing description and drawings represent the present invention, it will be obvious to those skilled in the art that various changes may be made therein without departing from the true spirit and scope of the present invention.

What is claimed is:

1. An atomizing device for atomic absorption spectroscopy according to the transverse Zeeman method, comprising:
   a tubular atomizing furnace with a horizontally oriented furnace tube which is transversely heated via furnace wings;
   said furnace being located with its furnace wings between vertically arranged electrodes and with its furnace tube transversely located between magnetic poles, so that liquid specimens for examination can be fed from the top and solid specimens for examination can be fed from the side.

2. The atomizing device according to claim 1, wherein the geometric center axes of the atomizing furnace and of the magnetic poles are displaced asymmetrically relative to one another.

3. The atomizing device according to claim 1, wherein the atomizing furnace is provided with a fill opening facing upward in the furnace tube and with a fill opening extending through a wing in the direction of a pipetting opening for examination of liquid, dissolved specimens.

4. The atomizing device according to claim 1, wherein, for examination of solid specimens, the atomizing furnace can be charged from the side and wherein a fill duct for the dissolved specimens is closed on the top of the furnace.

5. The atomizing device according to claim 1, wherein an insert which can be removed from the side is provided for geometric adaptation of the interior relationships of the atomizing device to a specimen feeder for solid specimens and for charging of the tubular portion of the furnace.

6. The atomizing device according to claim 1, wherein a measurement beam passes via windows arranged at the furnace tube and at least one inner protective gas flow Si is introduced via the window or window enclosure.

7. The atomizing device according to claim 1, wherein a duct leading up to the atomizing furnace extends below the atomizing furnace for at least one of: supplying the outer protective gas Sa and detecting the furnace temperature through radiation measurement.

8. The atomizing device according to claim 1, wherein outer and inner partial protective gas flows exit via a pipetting opening in liquids operation.

9. The atomizing device according to claim 1, wherein an inner partial protective gas flow which is introduced from the side of the atomizing device exits via a lateral charging side in solids operation.

* * * * *